(12) United States Patent
Koers

(10) Patent No.: US 12,416,023 B2
(45) Date of Patent: Sep. 16, 2025

(54) METHOD AND DEVICE FOR BIOLOGICAL PRODUCTION OF SULFURIC ACID

(71) Applicant: Bonno Koers, Doesburg (NL)

(72) Inventor: Bonno Koers, Doesburg (NL)

( * ) Notice: Subject to any disclaimer, the term of this patent is extended or adjusted under 35 U.S.C. 154(b) by 863 days.

(21) Appl. No.: 17/670,809

(22) Filed: Feb. 14, 2022

(65) Prior Publication Data

US 2023/0257782 A1    Aug. 17, 2023

(51) Int. Cl.
*C12P 3/00* (2006.01)
*C12M 1/00* (2006.01)
*C12M 1/12* (2006.01)
*C12N 1/20* (2006.01)

(52) U.S. Cl.
CPC ............... *C12P 3/00* (2013.01); *C12M 21/00* (2013.01); *C12M 23/06* (2013.01); *C12M 25/02* (2013.01); *C12M 29/18* (2013.01); *C12N 1/205* (2021.05)

(58) Field of Classification Search
CPC .......... C12P 3/00; C12M 21/00; C12M 23/06; C12M 25/02; C12M 29/18; C12M 25/18; C12N 1/205; C12N 1/20; C12R 2001/01
See application file for complete search history.

(56) References Cited

U.S. PATENT DOCUMENTS

| | | | |
|---|---|---|---|
| 6,194,198 B1 | 2/2001 | Koers | 435/266 |
| 6,610,268 B1 | 8/2003 | Young et al. | 423/522 |
| 2004/0023350 A1* | 2/2004 | Uhrie | C12P 3/00 |
| | | | 435/169 |
| 2010/0089818 A1 | 4/2010 | Koers | 210/488 |
| 2018/0311614 A1 | 11/2018 | Koers | B01D 53/85 |

OTHER PUBLICATIONS

Fetra & Yasui, Seiichi & Iwasaki, Masahiro & Yamashiro, Takaki & Ihara, Ikko & Umetsu, Kazutaka. (2020). Performance study of a bio-trickling filter to remove high hydrogen sulfide concentration from biogas: a pilot-scale experiment. Journal of Material Cycles and Waste Management. 22.10.1007/s10163-020-01031-4.

* cited by examiner

Primary Examiner — John McGuirk
(74) Attorney, Agent, or Firm — HAYES SOLOWAY P.C.

(57) ABSTRACT

Disclosed is a method and a device for biological production of sulfuric acid. The disclosure allows the use of high concentrations of sulfur as a feed for microbiological oxidation, resulting in high conversion of sulfur to sulfuric acid and, consequently, high sulfuric acid yields, which are obtained in an environmentally friendly way.

5 Claims, 2 Drawing Sheets

METHOD AND DEVICE FOR BIOLOGICAL PRODUCTION OF SULFURIC ACID

The present invention relates to a method and a device for biological production of sulfuric acid.

Sulfuric acid ($H_2SO_4$) is a universally used mineral acid which is produced and consumed in large quantities. Sulfuric acid is widely applied in agriculture in soil acidification. A high pH limits nutrient supply and plant growth. Sulfuric acid can be supplied to the soil to lower the soil pH and consequently improve crop performance. In particular for this application there is a strong need for biologically produced sulfuric acid in view of environmental considerations.

Prior art document U.S. Pat. No. 6,610,268 B1 discloses a method for microbiological production of sulfuric acid, which has low environmental impact.

The present inventor however considers that this prior art method has its limitations, in particular with respect to production efficiency. The present invention therefore aims at the provision of a method and device for producing sulfuric acid with low environmental impact with high production efficiency.

SUMMARY OF THE INVENTION

In a first aspect the invention relates to a method for biological production of sulfuric acid, comprising supplying an aqueous suspension containing sulfur oxidizing micro-organisms with a sulfur ($S_2$) feed, wherein said sulfur oxidizing micro-organisms produce sulfuric acid from said sulfur; trickling said sulfur fed suspension over a filter material covered with a biofilm of sulfur oxidizing micro-organisms; collecting the suspension trickled over said filter material in said reservoir in which aeration of the suspension takes place; recirculating of at least part of the collected suspension to the trickling step; and, when the suspension has reached a predetermined level of sulfuric acid, withdrawing part of the sulfuric acid enriched suspension from the reservoir as a product.

In a second aspect the invention relates to a device for biological production of sulfuric acid, comprising a filter material covered with a biofilm of sulfur oxidizing micro-organisms, and configured for trickling a sulfur fed aqueous suspension of sulfur oxidizing micro-organisms, wherein said sulfur oxidizing micro-organisms are capable of producing sulfuric acid from said sulfur; a reservoir configured for collection of said suspension from the filter material, wherein said reservoir comprises means for injecting air or any other oxygen source into the suspension contained in the reservoir; means for feeding sulfur to said suspension; means for recirculating said suspension from the reservoir to said filter material and means for withdrawing sulfuric acid enriched suspension from the reservoir as a product. The method of the first aspect can be carried out using the device of the second aspect. Therefore, any features and explanation disclosed in the present application relating to the method of the invention may also relate to the device of the invention and vice versa.

DETAILED DESCRIPTION OF THE INVENTION

Figure 1:
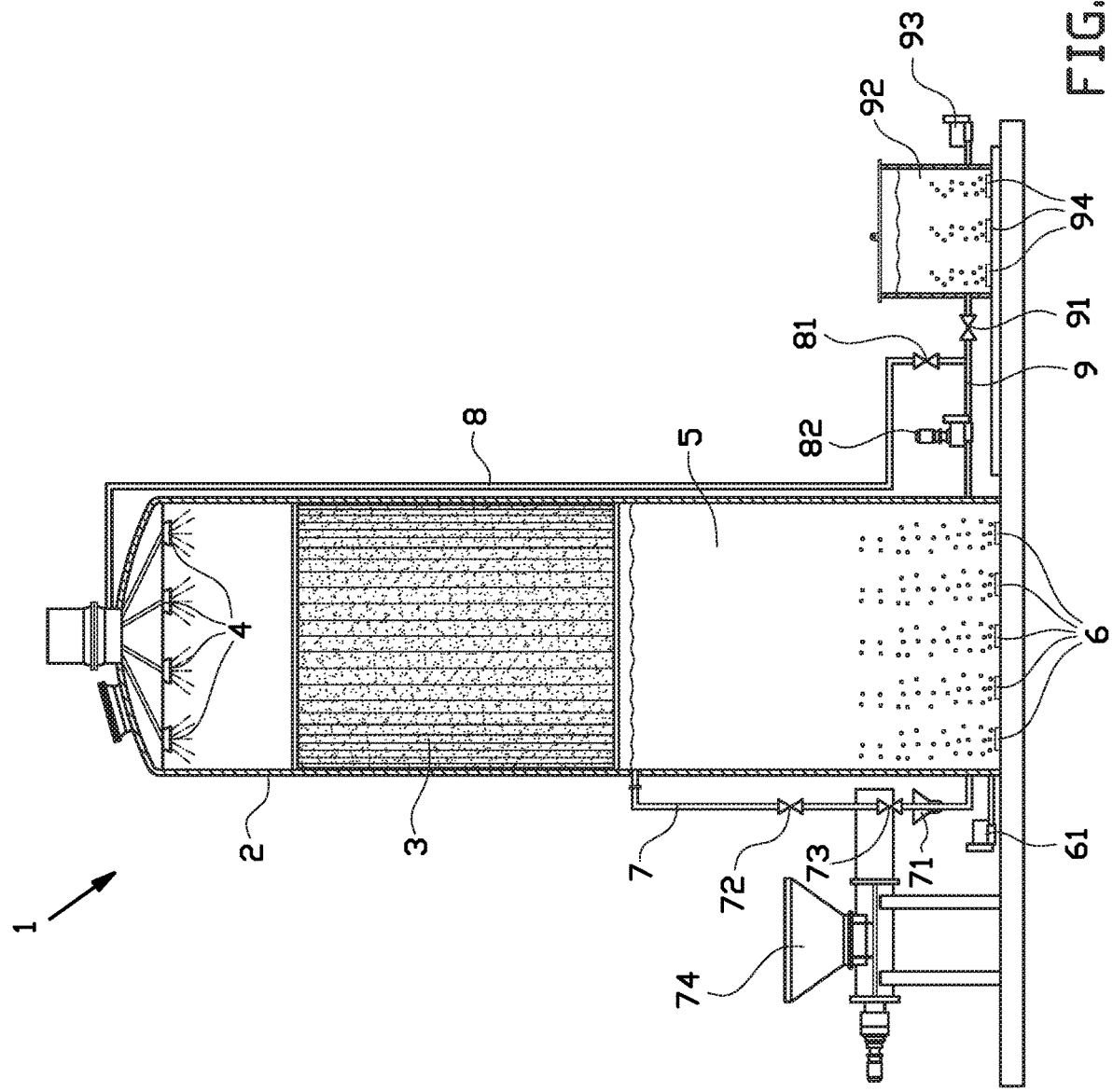
FIG. 1 shows a schematic cross-sectional view of an exemplary embodiment of the device according to the invention.

The present invention is based on the finding that microbiological production of sulfuric acid from sulfur can be improved by trickling a sulfur fed suspension over a filter material covered with a biofilm of said sulfur oxidizing micro-organisms, collecting the suspension trickled over said filter material in a downstream reservoir in which aeration of the suspension takes place; and recirculating the collected suspension to the trickling step. While prior art approaches such as described in U.S. Pat. No. 6,610,268 B1 disclose passing an aqueous solution with a sulfur material over an aerated pile of material with microbes capable of converting sulfur material to sulfuric acid and returning part of the stream for further contacting with the pile of packing material and part of the stream as acid product, the inventor has considered that this prior art approach has limitations with regard to efficiency, in particular when using elemental sulfur as a feed. In particular, the inventor has found that the amount of elemental sulfur that can be led over a packing material in a certain time period is limited in view of the dissolving capacity of sulfur.

The present invention solves this problem by collecting the suspension trickled down a filter material in a reservoir in which aeration of the suspension residing therein takes place. The term "aeration" in the context of the present invention should be understood as any procedure by which oxygen is added to the suspension. In practice, this preferably involves injecting air, for instance using injectors or spargers, although other oxygen containing gases may also be useful.

The reservoir is positioned downstream of the filter material. The inventor has found that the use of this aerated reservoir allows a high sulfur feed because it is ascertained that the sulfur remains in solution throughout the process. On the other hand the optimal aeration of the suspension in the filter material due to the open pores and flow channels therein and the aeration of the suspension in the reservoir ensure that the suspension has optimal oxygen levels at all times so that optimal oxidizing conditions for the microbial population in the suspension as well as the microbial population in the biofilms of the filter material are achieved. This on its turn results in optimal metabolization of sulfur to sulfuric acid. Because of this, clogging of filters due to sticky elemental sulfur which is thought to result from encapsulation of elemental sulfur in biofilms of sulfur oxidizing microorganisms under suboptimal conditions also does not take place because oxidation conditions are optimal and the sulfur remains in solution throughout the process. The invention herewith allows high concentrations of sulfur as a feed for microbiological oxidation, thus allowing high conversion of sulfur to sulfuric acid and, consequently, high sulfuric acid yields, which are obtained in an environmentally friendly way. In addition the device of the invention is of a user friendly design without the need for expensive and complicated equipment.

In principle the method of the invention only requires sulfur, water and microorganisms capable of producing sulfuric acid from sulfur.

Such microorganisms that are capable of oxidizing sulfur to sulfuric acid are well-known and include bacteria, such as the bacteria belonging to the *Thiobacillus* genus, such as

*Thiobacillus* thiooxidans. The same sulfur oxidizing microorganisms present in are biofilms and in the flowing suspension, allowing continuous oxidation of sulfur to sulfuric acid.

In order to allow efficient adherence of microorganisms the filter material is preferably made of a suitable plastic which also allows adherence of microorganisms. A preferred suitable plastic comprises polyethylene or polypropylene or a combination thereof.

Microorganisms adhere well to these materials and these plastics provide sufficient strength and flexibility, so that relatively thin sheets of material can be used, so that a higher surface per unit of volume can be used to be covered with microorganisms.

The filter material can be any filter material that is suitable for a biotrickling filter, i.e. that can be configured for trickling a sulfur fed aqueous suspension of sulfur oxidizing micro-organisms in the context of the invention. Examples of such filter materials include but are not limited to the materials discloses in patent documents U.S. Pat. No. 6,194, 198 B1, US 2010/089818 A1 and US 2018/311614 A1 of the present inventor. Although used therein for purposes of desulfurization of raw gases, the inventor has discovered that these filter materials are also applicable in the context of the present invention.

It is in particular preferred to use the biotrickling filter material of US 2018/311614 A1. In this respect it is preferred that the filter material comprises a first sheet of a plastic which is suitable for attachment of micro-organisms thereto, which has a planar surface; and a second sheet of a plastic which is suitable for attachment of micro-organisms thereto, has which a surface of undulations arranged in a parallel fashion with respect to each other; wherein said second sheet extends over the surface of the first sheet, wherein said second sheet is fixedly attached to the first sheet at the contact surface between the first sheet and each undulation of the second sheet, so that continuous channels are formed between the first and second sheet; wherein said filter material is rolled-up as a cylinder with open pores that are formed by said channels that along the continuous extend longitudinal axis of said cylinder. Because the undulated second sheet is fixedly attached to the first sheet which does not have undulations (flat sheet) at the contact surface between the first flat sheet and each undulation of the undulated sheet, the contact surfaces between the flat sheet and the undulated sheet cannot slide sidewards. This way the channels of consecutive sheets of a rolled up mat cannot slide into each other. The inventor has found that this has the effect that during rolling and packing of the material the channels remain their shape and dimensions, without losing flexibility so that the filter mat can easily be rolled into a cylinder. Because of this, predetermined dimensions of the channels designed for optimal flow are maintained at all times. This filter material has also increased strength compared to materials of similar construction wherein the flat and undulated sheets are not fixedly attached at the contact surfaces between the flat sheet and the undulated sheet. This makes the filter material of the invention easy to handle. Because the shape and dimensions of the channels are fixed at all time rolling and packing also does not require particular precautions to ensure acceptable channel dimensions.

Although the biotrickling filter and the reservoir may be contained in separate units in fluid communication with each other, for practical purposes it is preferred that the filter material and said reservoir are comprised in a single tower unit and that said filter material is arranged above said reservoir. This way the sulfur fed suspension can trickle down the filter material directly into the reservoir by gravity, which involves minimal input of energy and equipment. A suitable tower unit may suitably have an internal volume of 14-100 m$^3$. In such a tower a sulfur feed of x gram sulfur ($S_2$) per hour per cubic meter may yield 3×g or more sulfuric acid ($H_2SO_4$) per hour per cubic meter.

The reservoir is configured for collection of said suspension from the filter material, and comprises means for injecting air or any other oxygen containing gas into the suspension contained in the reservoir. In order to ensure optimal solubility of the sulfur supplied to the suspension it is preferred that the sulfur feed also is supplied to the suspension in said reservoir. The aeration of the suspension in the reservoir allows maximal amounts of sulfur dissolved in the solution and being available for the microorganisms in the suspension as well as the microorganisms in the biofilms of the filter material.

A sulfur feed solution or suspension may be prepared by dissolving $S_2$ in water before introducing the solution into the suspension of microorganisms in the device, such as in the reservoir. Alternatively, sulfur powder may be directly introduced into the reservoir.

For purposes of optimal solubility of sulfur in the suspension it is preferred that in the device of the invention said means for feeding sulfur feed to said suspension comprise an inlet in said reservoir to allow supply of sulfur, preferably a sulfur solution, into said reservoir. The means for feeding sulfur into the device of the invention may comprise any suitable means that allow injection of sulfur into the device, including dosing units, injectors, valves, etc. It is preferred that said means for feeding sulfur to said suspension comprise a Venturi-injector configured to inject a sulfur solution into the reservoir. Such a Venturi-injector allows injection of a sulfur solution under pressure, which is advantageous for mixing with the suspension in the reservoir and homogeneity of sulfur in the suspension, which on its turn increases access of the microorganisms to the sulfur.

In the reservoir aeration of the suspension takes place. This can be done with any means suitable to increase the oxygen concentration in the suspension in the reservoir. For this purpose preferably air is injected into the reservoir. This can suitably be realized by the use of injectors or spargers in the bottom of the reservoir. Accordingly, in the device of the invention said means for injecting air into the suspension contained in the reservoir may suitably comprise one or more injectors or spargers, which are preferably distributed on the bottom of the reservoir. These can be configured to bubble air from a source outside the device into the suspension in the reservoir.

In a starting phase of the sulfuric acid production process, the filter material can be grafted with microorganisms supplied with nutrients to allow formation of a biofilm on the filter material and to enable a quick start of the process of trickling the suspension down to the aerated reservoir and recycling the aerated suspension back to the trickling step. It is also possible to just circulate a suspension of microorganism and sulfur through the filter and reservoir. In due time the microorganisms will form biofilms on the filter material and will also continue to populate the circulating suspension.

In the starting phase the suspension may be recirculated for a time period of for instance several weeks in order to have satisfying levels of microorganisms and sulfuric acid. In this stage a product is not yet collected. Recirculation can be performed by means of conventional means such as tubings, pipes, pumps, valves, vents, etc. During the starting phase, the sulfur feed dosage should be adapted to the changing conditions in the suspension.

Once the process is stable in the sense that satisfying conversion of sulfur and production of sulfuric acid take place, sulfuric acid may be withdrawn from the process as a product. Useful levels of sulfuric acid in this respect may range from 3.5 wt. % of the suspension and higher.

Withdrawal of sulfuric acid enriched suspension can suitably be performed with conventional means. Withdrawal can be performed suitably with conventional means. A suitable way to withdraw sulfuric acid enriched product suspension is by opening a valve in a pipe between the reservoir and a collection tank. In other words, the sulfuric acid enriched product suspension can be simply drained from the reservoir to said collection tank or any other means for storage or further processing.

For purpose of withdrawal, at least part of the sulfuric acid enriched suspension is withdrawn—at certain intervals or continuously once the sulfuric acid concentration has reached a predetermined level—from the aerated reservoir as a product, while the other part of the suspension is recirculated to the filter material for the trickling step.

For the sake of continuity of the process it is preferred that any volume of sulfuric acid enriched suspension is compensated by the addition of an equal or at least essentially equal volume of sulfur feed.

Withdrawal at certain intervals can be done for instance after a period of low or absent sulfur feed to ensure high purity of sulfuric acid. Alternatively, the sulfur feed is continued.

In case of continuous withdrawal, the sulfur feed is preferably also continuous.

In case of continuous sulfur feed the withdrawn product contains a relatively high concentration of elemental sulfur. It is therefore preferred that the product suspension is collected into a collection tank, which is also aerated to provide conditions for the microorganisms in the suspension to metabolize remaining sulfur to sulfuric acid. Accordingly, the device may suitably comprise a collection tank in fluid communication with the reservoir and configured to receive withdrawn suspension from the reservoir, which comprises means for injecting air into the withdrawn suspension. The means for injecting air into the suspension contained in the collection tank may comprise one or more injectors or spargers, preferably distributed on the bottom of the collection tank.

DETAILED DESCRIPTION OF THE DRAWINGS

The method and device of the invention will now be explained with reference to FIG. 1. The following explanation is meant to illustrate and explain the invention and not to limit the claims.

FIG. 1 shows a schematic cross-sectional view of an exemplary embodiment of a device 1 according to the invention. The device is designed as a single tower 2 for biological production of sulfuric acid.

Tower 2 comprises in a top portion a filter material 3 covered with a biofilm of sulfur oxidizing microorganisms, and configured for trickling a sulfur fed aqueous suspension of sulfur oxidizing micro-organisms. Trickling is realized by means of sprayers 4. Once trickled down trough filter material 3, the suspension is collected in reservoir 5.

Reservoir 5 comprises multiple spargers 6 provided on the bottom. An aeration blower 61 is provided to provide air to the spargers 6 which bubble the air through the suspension contained in the reservoir 5.

A sulfur solution is fed to the suspension in the reservoir 5 via line 7. Line 7 may be equipped with a Venturi-injector 71 configured to inject a sulfur solution into the reservoir 5 via line 7. Such a Venturi-injector is advantageous for mixing with the suspension in the reservoir and homogeneity of sulfur in the suspension, which on its turn increases access of the microorganisms to the sulfur. Line 7 may be equipped with valves 72 and 73 and sulfur dosing unit 74 for suitably dosing the amount of elemental sulfur into the suspension in the reservoir 5.

Suspension is recirculated from the reservoir via lines 8 and 9 to sprayers 4 in order to trickle down filter material 3 again. Recirculation can be controlled using valves 81, 91 and pump 82.

After a starting phase in which microbiological populations grow and stabilize and the conversion of sulfur to sulfur acid has to start, sulfuric acid may be harvested as a product. Once the process is stable in the sense that satisfying conversion of sulfur and production of sulfuric acid take place and satisfying levels of sulfuric acid have been achieved, sulfuric acid may be withdrawn from the process as a product via line 9 using valve 91. For this purpose, at least part of the sulfuric acid enriched suspension is withdrawn from the aerated reservoir as a product at certain intervals or continuously, while the other part of the suspension is recirculated to the filter material via line 8 using valve 81 and pump 82 for the trickling step. Withdrawal of sulfuric acid enriched suspension from the reservoir as a product may also take place using pump 82 and withdrawn suspension may be collected in collection tank 92, which is aerated to provide conditions for the microorganisms in the suspension to metabolize remaining sulfur to sulfuric acid. For this purpose an aeration blower 93 is provided to provide air to a number of spargers 94 which bubble the air through the suspension contained in the collection tank 92.

In an exemplary tower corresponding to the one depicted in FIG. 1 with an internal volume of 14-100 $m^3$ a sulfur feed of x gram sulfur ($S_2$) per hour per cubic meter yielded 3×g sulfuric acid ($H_2SO_4$) per hour per cubic meter.

Figure 2A:
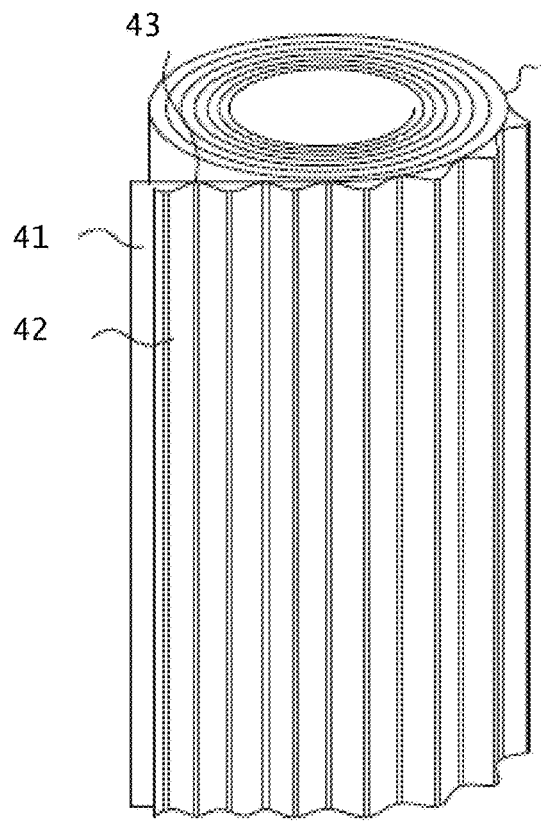
FIG. 2A shows a simplified representation of an embodiment of rolled-up filter material in accordance with the invention.
Figure 2B:
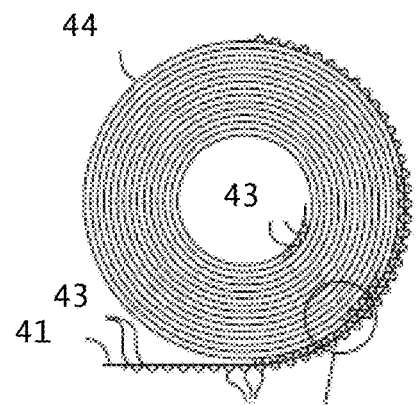
FIG. 2B shows a top view of this rolled up material and FIG. 2C shows an enlarged part of the top view of FIG. 2B.
Figure 2C:
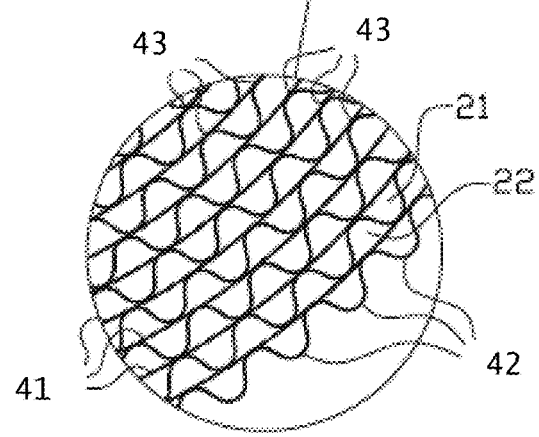

As shown in FIGS. 2A-C, the filter material 3 may be rolled for use to form a cylinder 44 with open pores formed by the continuous channels that extend along the longitudinal axis of said cylinder. From top view as shown in FIGS. 2B and 2C it can be seen that in the cylinder of FIG. 2A open pores (21, 22) are formed by the continuous channels that extend along the longitudinal axis of said cylinder. Because the undulated second sheet 42 is attached at the contact surface 43 between the first flat sheet 41 and each undulation of the undulated sheet 42, sliding of the contact surfaces 43 between the flat sheet 41 and the undulated sheet 42 is prevented so that the channels of consecutive sheets of a roll cannot slide into each other. Because of this predetermined dimensions of the channels designed for optimal flow and purification are maintained at all times, leading to increased surface area, lower exchange times of raw medium with microorganisms adhered to the surface of the channels, and increase of purification/polishing capacity.

The invention claimed is:

1. A method for biological production of sulfuric acid, comprising:

supplying an aqueous suspension containing sulfur oxidizing micro-organisms with a sulfur feed, wherein said sulfur oxidizing micro-organisms produce sulfuric acid from said sulfur;

trickling said sulfur fed suspension over a filter material covered with a biofilm of sulfur oxidizing micro-organisms;

collecting the suspension trickled over said filter material in a reservoir in which aeration of the suspension takes place;

recirculating of at least part of the collected suspension to the trickling step; and when the suspension has a predetermined level of sulfuric acid, withdrawing part of the sulfuric acid enriched suspension from the reservoir as a product.

2. The method according to claim 1, wherein said sulfur feed is supplied to the suspension in said reservoir.

3. The method according to claim 1, wherein said filter material comprises:
- a first sheet of a plastic which is suitable for attachment of micro-organisms thereto, which has a planar surface; and
- a second sheet of a plastic which is suitable for attachment of micro-organisms thereto, which has a surface of undulations arranged in a parallel fashion with respect to each other;

wherein said second sheet extends over the surface of the first sheet, wherein said second sheet is fixedly attached to the first sheet at the contact surface between the first sheet and each undulation of the second sheet, so that continuous channels are formed between the first and second sheet; and wherein said filter material is rolled-up as a cylinder with open pores that are formed by said continuous channels that extend along the longitudinal axis of said cylinder.

4. The method according to claim 1, wherein said sulfur fed suspension trickles over said filter material directly into said reservoir by gravity.

5. The method according to claim 1, wherein the suspension withdrawn from the reservoir is collected into a collection tank, which is aerated to provide conditions for the microorganisms in the suspension to metabolize remaining sulfur to sulfuric acid.

* * * * *